United States Patent
Li

(10) Patent No.: US 8,825,146 B2
(45) Date of Patent: *Sep. 2, 2014

(54) METHOD AND APPARATUS FOR CARDIAC ARRHYTHMIA CLASSIFICATION USING SAMPLE ENTROPY

(75) Inventor: Dan Li, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 851 days.

This patent is subject to a terminal disclaimer.

(21) Appl. No.: 12/349,274

(22) Filed: Jan. 6, 2009

(65) Prior Publication Data

US 2009/0118630 A1    May 7, 2009

Related U.S. Application Data

(63) Continuation of application No. 11/151,102, filed on Jun. 13, 2005, now Pat. No. 7,480,529.

(51) Int. Cl.
*A61B 5/046* (2006.01)

(52) U.S. Cl.
USPC .......................... 600/516; 600/518

(58) Field of Classification Search
USPC ................... 600/509, 513, 515–519
See application file for complete search history.

(56) References Cited

U.S. PATENT DOCUMENTS

| | | | |
|---|---|---|---|
| 5,191,524 A | | 3/1993 | Pincus et al. |
| 5,545,186 A | * | 8/1996 | Olson et al. ............. 607/14 |
| 5,817,132 A | | 10/1998 | Karagueuzian et al. |
| 5,846,189 A | | 12/1998 | Pincus |
| 6,192,273 B1 | | 2/2001 | Igel et al. |
| 6,480,734 B1 | | 11/2002 | Zhang et al. |
| 6,490,478 B1 | | 12/2002 | Zhang et al. |
| 6,597,943 B2 | | 7/2003 | Taha et al. |
| 6,694,188 B1 | | 2/2004 | Kroll |
| 2003/0069511 A1 | * | 4/2003 | Stridh et al. ............. 600/515 |

OTHER PUBLICATIONS

Lake et al., "Sample Entropy estimation using sampen", Nov. 1, 2004, PhysioToolkit, PhysioNet.*
"U.S. Appl. No. 11/151,102, Response filed Jun. 12, 2008 to Non-Final Office Action mailed Mar. 14, 2008", 14 pgs.
"U.S. Appl. No. 11/151,102 Non-Final Office Action mailed Mar. 14, 2008", 7 Pgs.

(Continued)

*Primary Examiner* — Kennedy Schaetzle
*Assistant Examiner* — Erica Lee
(74) *Attorney, Agent, or Firm* — Schwegman Lundberg & Woessner, P.A.

(57) ABSTRACT

An implantable medical device includes an arrhythmia detection and classification system that classifies an arrhythmia episode based on an irregularity parameter and/or a complexity parameter. The arrhythmia episode is detected from a cardiac signal. The irregularity parameter is indicative of the degree of cycle length irregularity of the cardiac signal and the complexity parameter is indicative of the degree of morphological complexity of the cardiac signal. One example of the irregularity parameter is an irregularity sample entropy, or a parameter related to the irregularity sample entropy, computed to indicate the cycle length irregularity. One example of the complexity parameter is a complexity sample entropy, or a parameter related to the complexity sample entropy, computed to indicate the morphological complexity. In one embodiment, the detected arrhythmia episode is classified using both the irregularity parameter and the complexity parameter.

18 Claims, 11 Drawing Sheets

(56) References Cited

OTHER PUBLICATIONS

Caswell Schuckers, S. A., et al., "Approximate entropy as a measure of morphologic variability for ventricular tachycardia and fibrillation", *Computers in Cardiology*, vol. 25, (1998), 265-268.

Caswell Schuckers, S. A., et al., "Distinction of Arrhythmias with the use of approximate entropy", *Computers in Cardiology*, vol. 26, (1999), 347-350.

Caswell Schuckers, S. A., "Use of approximate entropy measurements to classify ventricular tachycardia and fibrillation", *J Electrocardiol.*, 31 Suppl, (1998), 101-105.

Faes, L., "A method for quantifying atrial fibrillation organization based on wave-morphology similarity", *IEEE Transactions on Biomedical Engineering*, 49(12), (Dec. 2002), 1504-1513.

Lake, D E, et al., "Sample entropy analysis of neonatal heart rate variability", *Am J Physiol Requl Integr Comp Physiol*, 283(3), (2002), R789-797.

Richman, Joshua S, et al., "Physiological time-series analysis using approximate entropy and sample entropy", *Am J Physiol Circ Physiol*, vol. 278, (2000), H2039-H2049.

Signorini, M G, et al., "Regularity patterns in heart rate variability signal: the approximate entropy approach", *Proceedings of the 20th Annual International Conference of the IEEE Engineering in Medicine and Biology Society, IEMBS*, (1998), 306-309.

Sih, H J, et al., "A high-temporal resolution algorithm for quantifying organization during atrial fibrillation", *IEEE Transactions on Biomedical Engineering*, 46(4), (1999), 440-450.

Swerdlow, C D, et al., "Detection of Atrial Fibrillation and Flutter by a Dual-Chamber Implantation Cardioverter-Defibrillator", *Circulation*, 101(8), (Feb. 28, 2000), 878-885.

Wang, K, et al., "Approximate entropy based pulse variability analysis", *16th IEEE Symposium Computer-Based Medical Systems, 2003. Proceedings.*, (2003), 236-241.

Xu, W, et al., "New Bayesian discriminator for detection of atrial tachyarrhythmias", *Circulation*, 105(12), (2002), 1472-1479.

\* cited by examiner

METHOD AND APPARATUS FOR CARDIAC ARRHYTHMIA CLASSIFICATION USING SAMPLE ENTROPY

CROSS REFERENCE TO RELATED APPLICATION

This application is a continuation of U.S. application Ser. No. 11/151,102, filed Jun. 13, 2005, now issued as U.S. Pat. No. 7,480,529, which is hereby incorporated by reference in its entirety.

TECHNICAL FIELD

This document relates generally to cardiac rhythm management (CRM) systems and particularly, but not by way of limitation, to such a system providing for classification of arrhythmias based on cycle length irregularity and morphological complexity of a cardiac signal.

BACKGROUND

The heart is the center of a person's circulatory system. The left portions of the heart, including the left atrium and left ventricle, draw oxygenated blood from the lungs and pump it to the organs of the body to provide the organs with their metabolic needs for oxygen. The right portions of the heart, including the right atrium and right ventricle, draw deoxygenated blood from the body organs and pump it to the lungs where the blood gets oxygenated. These mechanical pumping functions are accomplished by contractions of the heart. In a normal heart, the sinoatrial node, the heart's natural pacemaker, generates electrical impulses that travel through normal electrical conduction pathways to cause the atria, and then the ventricles, to contract.

Tachyarrhythmia occurs when electrical impulses are generated from one or more abnormal electrical foci and/or when abnormal electrical conduction loops are formed in the heart. When tachyarrhythmia occurs, the heart contracts at a rate higher than a normal heart rate. When the heart rate rises beyond a certain point, the atria and/or the ventricles do not have sufficient time to be filled with blood before each contraction occurs. Consequently, the heart fails to pump sufficient blood to the body organs to meet their metabolic demand. Tachycardia, such as atrial flutter (AFL) or ventricular tachycardia (VT), occurs when the heart contracts at a tachyarrhythmia rate with a substantially regular rhythm. Fibrillation, such as atrial fibrillation (AF) or ventricular fibrillation (VF), occurs when the heart contracts at a tachyarrhythmia rate with a substantially irregular rhythm. VF is a life threatening condition requiring immediate medical treatment such as ventricular defibrillation. AF, though not directly life threatening, also needs medical treatment such as atrial defibrillation to restore a normal cardiac function and to prevent the deterioration of the heart.

Implantable medical devices such as implantable cardioverter/defibrillators (ICDs) are used to treat tachyarrhythmias, including tachycardia and fibrillation. ICDs are capable of delivering defibrillation shock pulses. Various types of ICD are also capable of delivering pacing pulses. Because a defibrillation shock pulse carries a substantial amount of energy and causes substantial discomfort to the patient, it is to be used only when considered necessary. For example, a known type ICD delivers anti-tachycardia pacing (ATP) therapy in response to a detection of tachycardia. Only if the ATP therapy fails to restore a normal cardiac rhythm, a defibrillation shock pulse is delivered. In response to a detection of fibrillation, on the other hand, a defibrillation shock pulse is delivered without delivering the ATP therapy.

Thus, to determine a suitable type of therapy in response to a detection of tachyarrhythmia, there is a need to classify that tachyarrhythmia, such as by discriminating between tachycardia and fibrillation.

SUMMARY

An implantable medical device includes an arrhythmia detection and classification system that classifies an arrhythmia episode based on an irregularity parameter and/or a complexity parameter. The arrhythmia episode is detected from a cardiac signal. The irregularity parameter is indicative of the degree of cycle length irregularity of the cardiac signal and the complexity parameter is indicative of the degree of morphological complexity of the cardiac signal. One example of the irregularity parameter is an irregularity sample entropy, or a parameter related to the irregularity sample entropy, computed to indicate the cycle length irregularity. One example of the complexity parameter is a complexity sample entropy, or a parameter related to the complexity sample entropy, computed to indicate the morphological complexity.

In one embodiment, a system for classifying cardiac arrhythmias includes a signal input, an irregularity analyzer, a complexity analyzer, and an arrhythmia classifier. The signal input receives a cardiac signal indicative of an arrhythmia episode. The irregularity analyzer produces an irregularity parameter indicative of a degree of cycle length irregularity of the cardiac signal. The complexity analyzer produces a complexity parameter indicative of a degree of morphological complexity of the cardiac signal. The arrhythmia classifier classifies the arrhythmia episode based on the irregularity parameter and the complexity parameter.

In one embodiment, a method for classifying cardiac arrhythmias is provided. An arrhythmia episode is detected. A cardiac signal indicative of the arrhythmia episode is received. An irregularity parameter indicative of a degree of cycle length irregularity of the cardiac signal is computed. A complexity parameter indicative of a degree of morphological complexity of the cardiac signal is computed. The arrhythmia episode is classified based on the irregularity parameter and the complexity parameter.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

The drawings, which are not necessarily drawn to scale, illustrate generally, by way of example, but not by way of limitation, various embodiments discussed in the present document.

DETAILED DESCRIPTION

Figure 1:
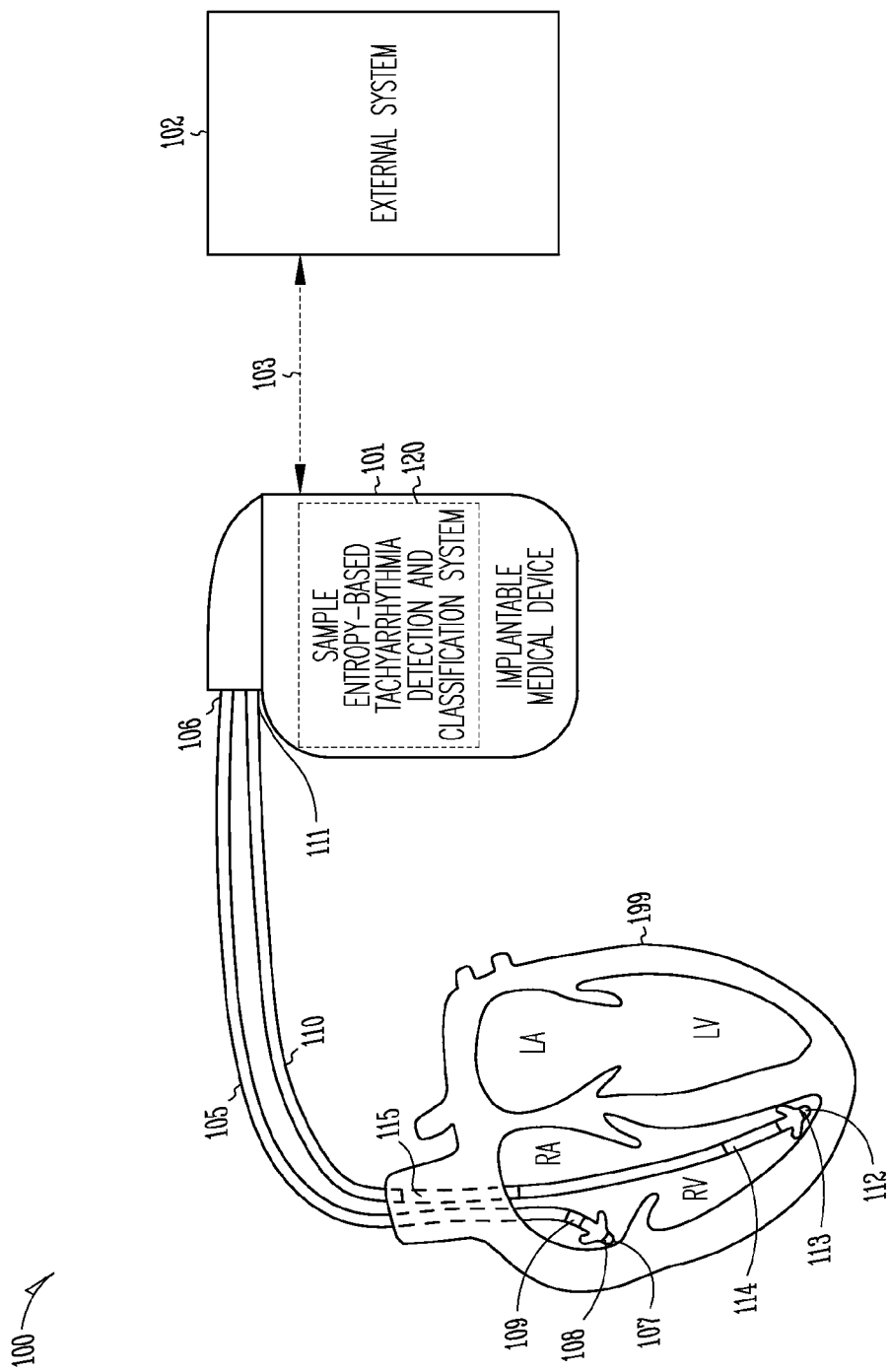
FIG. 1 is an illustration of one embodiment of a CRM system and portions of the environment in which the CRM system operates.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that the embodiments may be combined, or that other embodiments may be utilized and that structural, logical and electrical changes may be made without departing from the spirit and scope of the present invention. References to "an", "one", or "various" embodiments in this disclosure are not necessarily to the same embodiment, and such references contemplate more than one embodiment. The following detailed description provides examples, and the scope of the present invention is defined by the appended claims and their legal equivalents.

This document discusses, among other things, a tachyarrhythmia detection and classification system that classifies tachyarrhythmias based on cycle length irregularity and/or morphological complexity of a cardiac signal. The classification of a detected tachyarrhythmia episode provides a basis for selecting a suitable therapy, when needed, to terminate that tachyarrhythmia episode. In one embodiment, the system analyzes the degree of cycle length irregularity of the cardiac signal and the degree of morphological complexity of the cardiac signal and discriminates between tachycardia and fibrillation when at least one of the degree of cycle length irregularity and the degree of morphological complexity exceeds a limit. In one embodiment, an irregularity sample entropy, or a parameter related to the irregularity sample entropy, is computed to indicate the cycle length irregularity. In one embodiment, a complexity sample entropy, or a parameter related to the complexity sample entropy, is computed to indicate the morphological complexity. In one embodiment, the system computes an irregularity parameter indicative of the degree of cycle length irregularity and a complexity parameter indicative of the degree of morphological complexity.

The relationship between a heart rate and a cardiac cycle length (also known as cardiac interval), as used in this document, is the relationship between a frequency and its corresponding period. If a heart rate is given in beats per minute (bpm), its corresponding cardiac cycle length in milliseconds is calculated by dividing 60,000 by the heart rate (where 60,000 is the number of milliseconds in a minute). Any process, such as a comparison, using a heart rate is to be modified accordingly when a cardiac cycle length is used instead. For example, if a tachyarrhythmia is detected when the ventricular rate exceeds a tachyarrhythmia threshold rate, an equivalent process is to detect the tachyarrhythmia when the ventricular cycle length falls below a tachyarrhythmia threshold interval. The appended claims should be construed to cover such variations.

FIG. 1 is an illustration of one embodiment of a CRM system 100 and portions of the environment in which CRM system 100 operates. CRM system 100 includes an implantable medical device 101 that is electrically coupled to a heart 199 through leads 105 and 110. An external system 102 communicates with implantable medical device 101 via a telemetry link 103. In one embodiment, implantable medical device 101 is an ICD. In a specific embodiment, implantable medical device 101 is an ICD that has pacing capabilities. In various embodiments, implantable medical device 101 includes a cardioversion/defibrillation circuit and one or more additional therapeutic and/or monitoring circuits and/or devices. Examples of such therapeutic and/or monitoring circuits and/or devices include a pacing circuit, a neural stimulation circuit, a drug delivery device, a drug delivery controller, a biologic therapy delivery device, and a biologic therapy controller.

Implantable medical device 101 includes a hermetically sealed can housing an electronic circuit that senses physiological signals and delivers therapeutic electrical pulses. The hermetically sealed can also functions as an electrode for sensing and/or pulse delivery purposes. In one embodiment, as illustrated in FIG. 1, the electronic circuit senses at least an atrial electrogram and a ventricular electrogram from heart 199 and delivers pacing and cardioversion/defibrillation pulses to heart 199. Lead 105 is a pacing lead that includes a proximal end 106 connected to implantable medical device 101 and a distal end 107 disposed in the right atrium (RA) of heart 199. A pacing-sensing electrode 108 is located at distal end 107. Another pacing-sensing electrode 109 is located near distal end 107. Electrodes 108 and 109 are electronically connected to implantable medical device 101 via separate conductors in lead 105 to allow sensing of the atrial electrogram and/or delivery of atrial pacing pulses. Lead 110 is a defibrillation lead that includes a proximal end 111 connected to implantable medical device 101 and a distal end 112 disposed in the right ventricle (RV) of heart 199. A pacing-sensing electrode 113 is located at distal end 112. A defibrillation electrode 114 is located near distal end 112 but electrically separated from pacing-sensing electrode 113. Another defibrillation electrode 115 is located at a distance from distal end 112 for supraventricular placement. Electrodes 113, 114, and 115 are electrically connected to implantable medical device 101 via separate conductors in lead 110. Electrode 113 allows sensing of the ventricular electrogram and/or delivery of ventricular pacing pulses. Electrodes 114 and 115 allow delivery of cardioversion/defibrillation pulses. In various embodiments, system 101 includes one or more leads each including one or more electrodes, depending on the requirements of the intended therapy and the functions of implantable medical device 101. Leads 105 and 110 are illustrated as examples of such leads. Another example is an atrial lead similar to lead 105 with one or more electrodes configured for delivering atrial cardioversion/defibrillation pulses.

Implantable medical device 101 includes a sample entropy-based tachyarrhythmia detection and classification system 120 that includes a sample entropy-based tachyarrhythmia classification module. The sample entropy-based tachyarrhythmia classification module discriminates between tachycardia and fibrillation based on a degree of irregularity and/or a degree of complexity of a cardiac signal such as the atrial electrogram or the ventricular electrogram. The degree of irregularity and the degree of complexity are each indicated by a sample entropy or a parameter related to the sample entropy. Depending on the outcome of the tachyarrhythmia detection and classification, system 120 determines whether to deliver a pacing and/or cardioversion/defibrillation therapy. In one embodiment, sample entropy-based tachyarrhythmia detection and classification system 120 classifies a detected atrial tachyarrhythmia by discriminating between AFL and AF. If the detected tachyarrhythmia is classified as AFL, implantable medical device 101 delivers an atrial ATP. If the detected tachyarrhythmia is classified as AF, implantable medical device 101 delivers an atrial defibrillation pulse. In one embodiment, sample entropy-based tachyarrhythmia detection and classification system 120 classifies a detected tachyarrhythmia by discriminating between VT and VF. If the detected tachyarrhythmia is classified as VT, implantable medical device 101 delivers a ventricular ATP. If the detected tachyarrhythmia is classified as VF, implantable medical device 101 delivers a ventricular defibrillation pulse.

External system 102 allows for programming of implantable medical device 101 and receives signals acquired by implantable medical device 101. In one embodiment, external system 102 includes a programmer. In another embodiment, external system 102 is a patient management system including an external device in proximity of implantable medical device 101, a remote device in a relatively distant location, and a telecommunication network linking the external device and the remote device. The patient management system allows access to implantable medical device 101 from a remote location, such as for monitoring patient status and adjusting therapies. In one embodiment, telemetry link 103 is an inductive telemetry link. In an alternative embodiment, telemetry link 103 is a far-field radio-frequency telemetry link. Telemetry link 103 provides for data transmission from implantable medical device 101 to external system 102. This may include, for example, transmitting real-time physiological data acquired by implantable medical device 101, extracting physiological data acquired by and stored in implantable medical device 101, extracting therapy history data stored in implantable medical device 101, and extracting data indicating an operational status of implantable medical device 101 (e.g., battery status and lead impedance). Telemetry link 103 also provides for data transmission from external system 102 to implantable medical device 101. This may include, for example, programming implantable medical device 101 to acquire physiological data, programming implantable medical device 101 to perform at least one self-diagnostic test (such as for a device operational status), and programming implantable medical device 101 to deliver pacing and/or cardioversion/defibrillation therapies.

Figure 2:
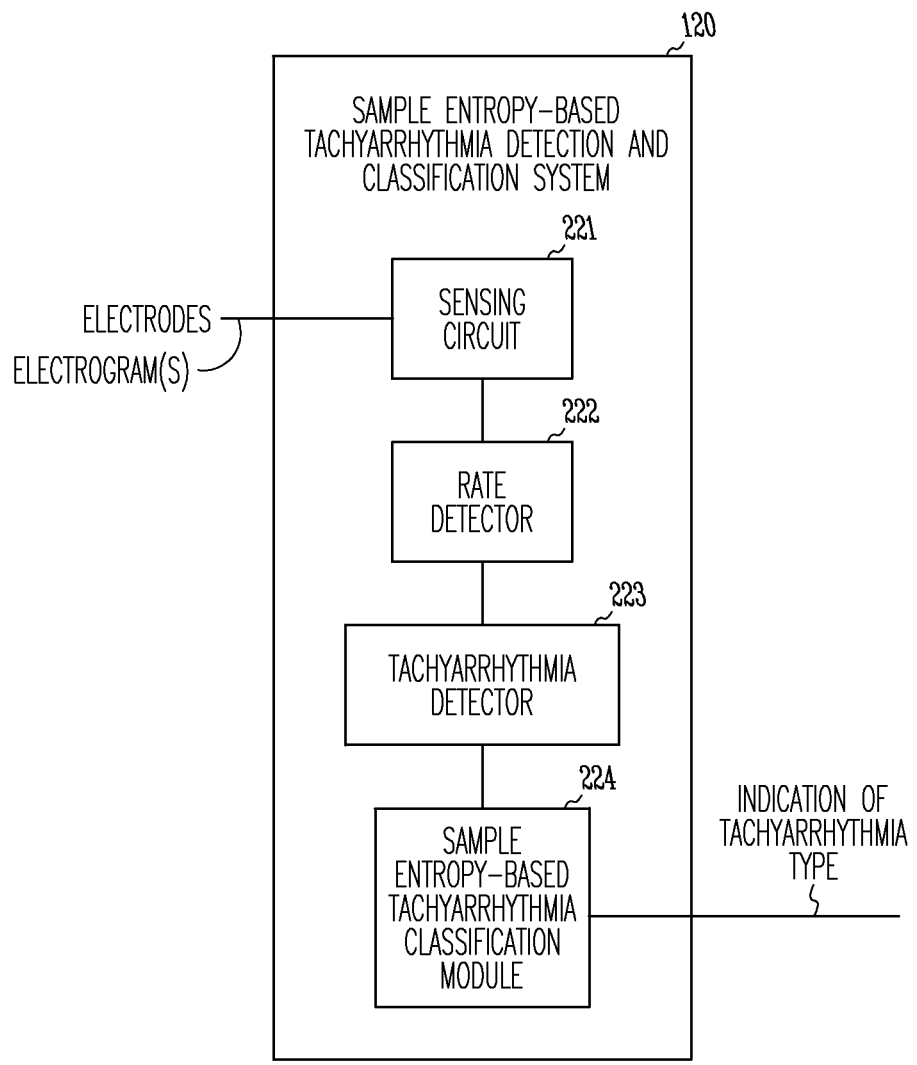
FIG. 2 is a block diagram illustrating an embodiment of a sample entropy-based tachyarrhythmia detection and classification system that is part of the CRM system.

FIG. 2 is a block diagram illustrating an embodiment of sample entropy-based tachyarrhythmia detection and classification system 120. System 120 includes a sensing circuit 221, a rate detector 222, a tachyarrhythmia detector 223, and a sample entropy-based tachyarrhythmia classification module 224. Sensing circuit 221 is electrically coupled to heart 199 through one or more electrodes to sense atrial and/or ventricular electrograms. The atrial electrogram includes atrial events each indicative of an atrial depolarization, also known as a P-wave. The ventricular electrogram includes ventricular events each indicative of a ventricular depolarization, also known an R-wave. Rate detector 222 detects an atrial rate based on the atrial electrogram and/or a ventricular rate based on the ventricular electrogram. The atrial rate is the frequency of occurrence of the atrial events. The ventricular rate is the frequency of occurrence of the ventricular events. In one embodiment, the atrial and ventricular rates are each expressed in beats per minute (bpm), i.e., number of detected atrial or ventricular depolarizations per minute. Tachyarrhythmia detector 223 detects a tachyarrhythmia based on at least one of the atrial rate and the ventricular rate. In one embodiment, the tachyarrhythmia is detected when the atrial rate exceeds a predetermined tachyarrhythmia threshold rate. In another embodiment, the tachyarrhythmia is detected when the ventricular rate exceeds a predetermined tachyarrhythmia threshold rate. In one embodiment, tachyarrhythmia detector 223 further determines whether the tachyarrhythmia is an atrial tachyarrhythmia or a ventricular tachyarrhythmia. Sample entropy-based tachyarrhythmia classification module 224 classifies the detected tachyarrhythmia as one of tachycardia and fibrillation.

In one embodiment, system 120 is part of an atrial defibrillation device. Sensing circuit 221 senses an electrogram indicative of atrial tachyarrhythmia. Rate detector 222 detects an atrial rate based on that electrogram. Tachyarrhythmia detector 223 detects an atrial tachyarrhythmia based on the atrial rate. Sample entropy-based tachyarrhythmia classification module 224 classifies the detected atrial tachyarrhythmia as one of AFL and AF.

In one embodiment, system 120 is part of a ventricular defibrillation device. Sensing circuit 221 senses an electrogram indicative of ventricular tachyarrhythmia. Rate detector 222 detects a ventricular rate based on that electrogram. Tachyarrhythmia detector 223 detects a ventricular tachyarrhythmia based on the ventricular rate. Sample entropy-based tachyarrhythmia classification module 224 classifies the detected ventricular tachyarrhythmia as one of VT and VF.

Figure 3:
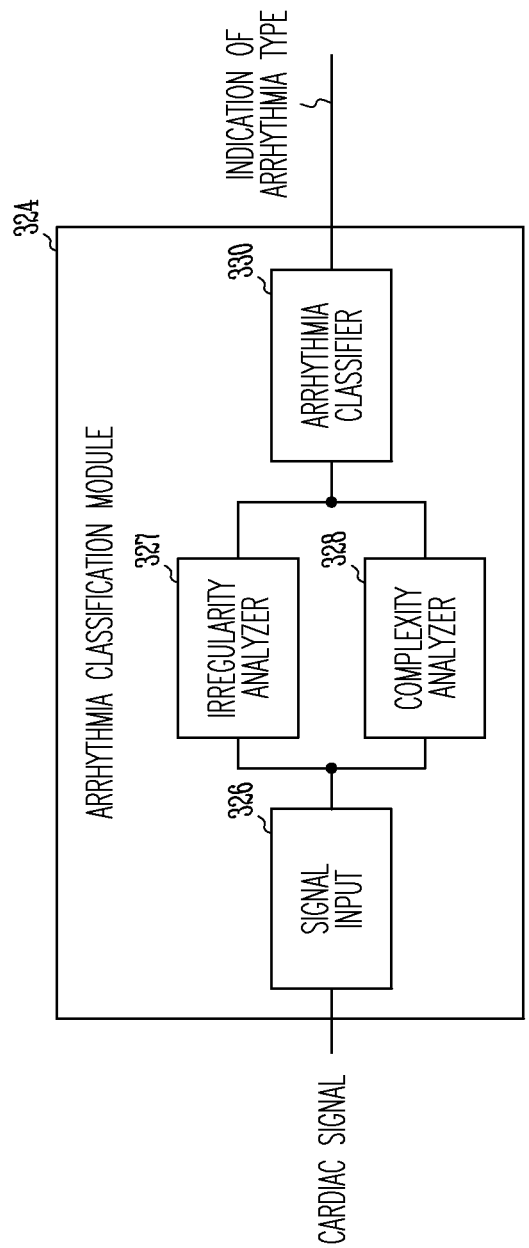
FIG. 3 is a block diagram illustrating an embodiment of an arrhythmia classification module.

FIG. 3 is a block diagram illustrating an embodiment of an arrhythmia classification module 324. Arrhythmia classification module 324 includes a signal input 326, an irregularity analyzer 327, a complexity analyzer 328, and an arrhythmia classifier 330. Signal input 326 receives a cardiac signal indicative of a detected arrhythmia episode. Irregularity analyzer 327 produces an irregularity parameter indicative of the degree of cycle length irregularity of the cardiac signal. Complexity analyzer 328 produces a complexity parameter indicative of the degree of morphological complexity of the cardiac signal. Arrhythmia classifier 330 classifies the detected arrhythmia episode based on the irregularity parameter and the complexity parameter.

In one embodiment, arrhythmia classification module 324 performs a sample entropy computation to produce the irregularity parameter and the complexity parameter. The irregularity parameter and the complexity parameter are each a sample entropy or a parameter related to the sample therapy. In this embodiment, sample entropy-based tachyarrhythmia classification module 224 is a specific embodiment of arrhythmia classification module 324.

Sample Entropy (SampEn)

Sample entropy (SampEn) is a statistical measure of irregularity or complexity of a signal or system. A smaller SampEn indicates a lower degree of irregularity or a lower degree of complexity. A larger SampEn indicates a higher degree of irregularity or a higher degree of complexity. Examples of using SampEn in physiological signal analysis, including the advantages, are discussed in Lake et al., *Am. J. Physiol. Regul. Integr. Comp. Physiol.*, 283: R789-97 (2002) and Richman et al., *Am. J. Physiol. Heart Circ. Physiol*, 278: H2039-49 (2000).

SampEn is computed for a signal recorded over a certain length of time to indicate the degree of irregularity and/or the degree of complexity of that signal. The signal is digitized into a sequence of n samples: u(1), u(2), . . . u(n). In one embodiment, the sequence is a sequence of scalars, i.e., each sample u(i) is a scalar. In another embodiment, the sequence is a sequence of vectors, i.e., each sample u(i) is a vector of p scalars: $u(i)=[u_1(i), u_2(i), \ldots u_p(i)]$. The following discussion of SampEn computation applies for u(1), u(2), . . . u(n) being either a set of n scalars or a set of n vectors.

The sequence is divided into n−m+1 signal segments each including m samples and given as $x_m(i)=[u(i), u(i+1), \ldots u(i+m-1)]$, where 1≤i≤(n−m+1), and m is a number smaller than n and represents the length of each signal segment. A vector matching score $D_m(i, j)$ between $x_m(j)$ and $x_m(i)$ (j≠i), which provides for a measure of similarity between the two signal segments, is given as follows:

$$D_m(i, j) := \begin{cases} 1, & L[x_m(j), x_m(i)] \leq r; \\ 0, & \text{otherwise,} \end{cases} \quad (1)$$

where L is the maximum difference between corresponding components of signal segment $x_m(j)$ and $x_m(i)$, given by:

$$L[x_m(j), x_m(i)] = \max_{k=0 \sim m-1} \{L[u(j+k), u(i+k)]\}, \quad (2)$$

and r is a threshold. In one embodiment, the parameters n, m, and r are each empirically determined. L indicates the similarity between signal segments $x_m(j)$ and $x_m(i)$.

In one embodiment, SampEn is given by:

$$SampEn(n, m, r) = -\ln[\Gamma(n, m, r)], \quad (3)$$

where:

$$\Gamma(n, m, r) := \frac{\sum_{i=1}^{n-m-1} \sum_{j=i+1}^{n-m} D_{m+1}(i, j)}{\sum_{i=1}^{n-m-1} \sum_{j=i+1}^{n-m} D_m(i, j)} \in [0, 1]. \quad (4)$$

In one embodiment, SampEn is a parameter used to indicate the degree of irregularity or complexity of the signal recorded over the certain length of time. SampEn is compared with a predetermined entropy threshold θ. If SampEn exceeds θ, then a detection of irregularity or complexity (i.e., a high degree of irregularity or complexity) is indicated. If SampEn does not exceed θ, then no detection of irregularity or complexity is indicated. In another embodiment, Γ is a parameter used to indicate the degree of irregularity or complexity. Γ is compared with a predetermined threshold γ. If Γ does not exceed γ, then a detection of irregularity or complexity (i.e., a high degree of irregularity or complexity) is indicated. If Γ exceeds γ, then no detection of irregularity or complexity is indicated. Using Γ instead of SampEn reduces the amount of computation by eliminating the logarithmic computation step.

Figure 4:
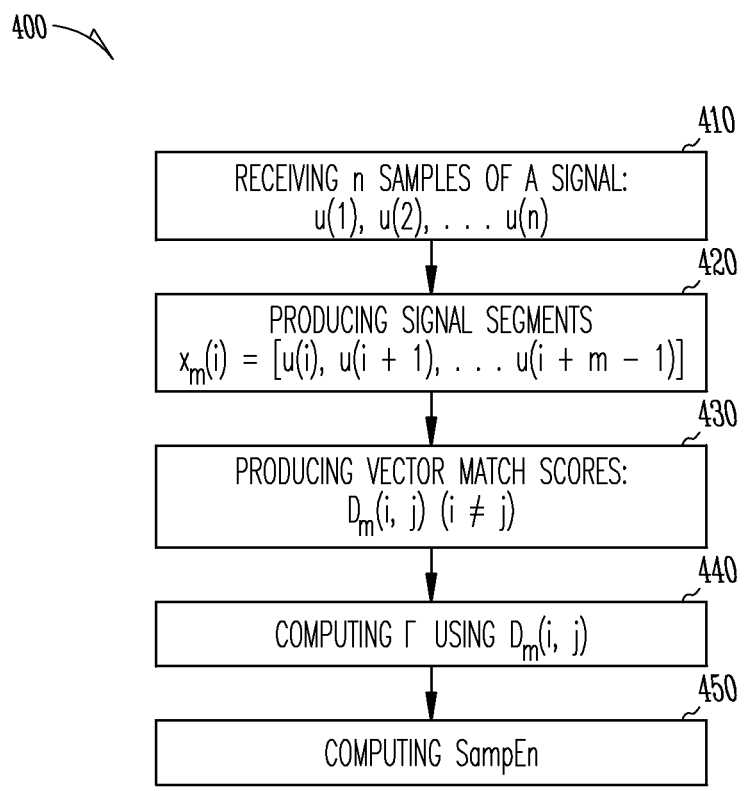
FIG. 4 is a flow chart illustrating an embodiment of a method for computing sample entropy.

FIG. 4 is a flow chart illustrating an embodiment of a method 400 for computing sample entropy for the purpose of classifying a detected arrhythmia. In one embodiment, SampEn is the parameter used in the classification of arrhythmia. In another embodiment, Γ, which is a parameter related to SampEn as discussed above, is the parameter used in the classification of arrhythmia.

Samples of a signal, u(1), u(2), . . . u(n), are received at 410. The samples are taken from a cardiac signal. To analyze the cycle length irregularity, the n samples u(1), u(2), . . . u(n) are a set of n scalars each representing a cardiac cycle length measured from the cardiac signal. To analyze the morphological complexity, the n samples u(1), u(2), . . . u(n) are a set of n vectors each representing a set of morphological features related to a cardiac cycle and extracted from the cardiac signal.

Signal segments each including m samples, $x_m(i)=[u(i), u(i+1), \ldots u(i+m-1)]$, where 1≤i≤n−m+1, are produced at 420. The number m is a predetermined number smaller than n. This results in n−m+1 signal segments.

Vector match scores $D_m(i, j)$, are produced for all pairs of i and j, where i≠j, at 430, using Equations (1) and (2) and threshold r. The pairs of i and j includes all combination of (i, j) where 1≤i≤n−m+1, 1≤j≤n−m+1, and i≠j.

The parameter Γ is computed using $D_m(i, j)$ according to Equation (4) at 440. The parameter Γ is related to SampEn by the relationship given by Equation (3). In one embodiment, Γ is the parameter used in the classification of arrhythmia, and there is no need to proceed to step 450 after step 440 is completed.

SampEn is computed using by using Γ according to Equation (3) at 450. In one embodiment, SampEn is the parameter used in the classification of arrhythmia.

Figure 5:
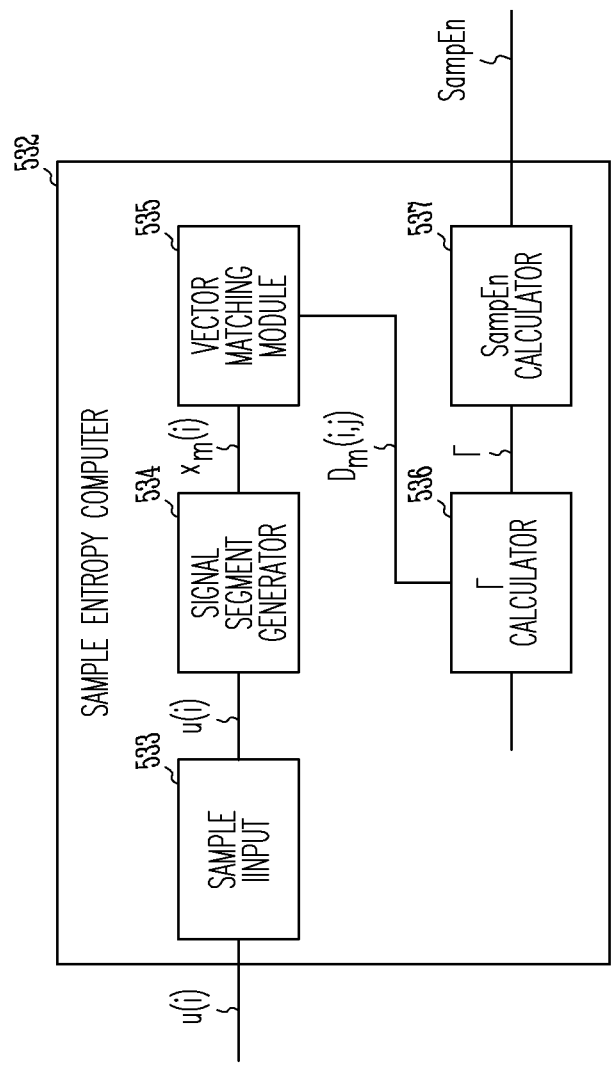
FIG. 5 is a block diagram illustrating an embodiment of a sample entropy computer.

FIG. 5 is a block diagram illustrating an embodiment of sample entropy computer 532. Sample entropy computer 532 performs method 400 for the classification of arrhythmia. In one embodiment, as illustrated in FIG. 5, SampEn is the parameter used in the classification of arrhythmia, and entropy computer 532 includes a sample input 533 that performs step 410, a signal segment generator 534 that performs step 420, a vector matching module 535 that performs step 430, a Γ calculator 536 that performs step 440, and a SampEn calculator 537 that performs step 450. In another embodiment, Γ is the parameter used in the classification of arrhythmia, and entropy computer 532 includes a sample input 533 that performs step 410, a signal segment generator that performs step 420, a vector matching module that performs step 430, and a Γ calculator that performs step 440.

Arrhythmia Classification Based on Irregularity Sample Entropy (SampEn$_I$)

Figure 6:
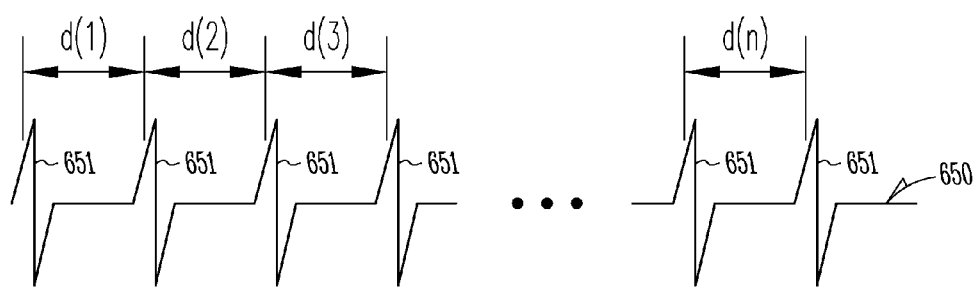
FIG. 6 illustrates an embodiment of a method for sampling a cardiac signal for analyzing cycle length irregularity of the cardiac signal using sample entropy.

FIG. 6 illustrates an embodiment of a method for sampling a cardiac signal 650 for analyzing the cycle length irregularity of the cardiac signal using sample entropy. Cardiac signal 650 includes cardiac depolarizations 651 and is indicative of a tachyarrhythmia. In one embodiment, cardiac signal 650 is an atrial electrogram, and cardiac depolarizations 651 are each an atrial depolarization (P-wave). In another embodiment, cardiac signal 650 is a ventricular electrogram, and cardiac depolarizations 651 are each a ventricular depolarization (R-wave). Cardiac cycle lengths d(1), d(2), . . . d(n) are each a time interval between two adjacent cardiac depolarizations.

Figure 7:
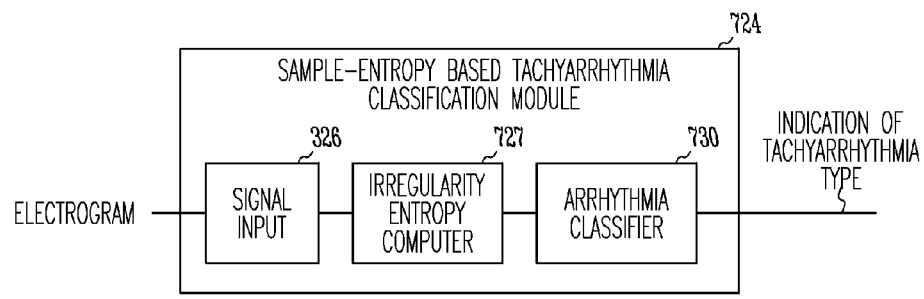
FIG. 7 is a block diagram illustrating an embodiment of a sample entropy-based tachyarrhythmia classification module.

FIG. 7 is a block diagram illustrating a sample entropy-based tachyarrhythmia classification module 724. Sample entropy-based tachyarrhythmia classification module 724 is a specific embodiment of sample entropy-based tachyarrhythmia classification module 224 and classifies tachyarrhythmias by analyzing the cycle length irregularity of cardiac signal 650. Sample entropy-based tachyarrhythmia classification module 724 includes signal input 326, an irregularity entropy computer 727, and an arrhythmia classifier 730. Irregularity entropy computer 727 is a specific embodiment of irregularity analyzer 327 and includes a sample entropy computer that performs method 400 by using the cardiac cycle lengths d(1), d(2), . . . d(n) as sample points u(1), u(2), . . . u(n). The resultant irregularity $\Gamma$ ($\Gamma_I$) or irregularity sample entropy (SampEn$_I$) indicates the degree of cycle length irregularity of cardiac signal 650. Arrhythmia classifier 730 classifies the tachyarrhythmia indicated in cardiac signal 650 as one of tachycardia and fibrillation based on $\Gamma_I$ or SampEn$_I$. In one embodiment, cardiac signal 650 is indicative of tachyarrhythmia, arrhythmia classifier 730 classifies the tachyarrhythmia as fibrillation if $\Gamma_I$ is below a predetermined threshold $\gamma_I$ or if SampEn$_I$ exceeds a predetermined threshold $\theta_I$ and as tachycardia if $\Gamma_I$ exceeds $\gamma_I$ or if SampEn$_I$ is below $\theta_I$. In a specific embodiment, cardiac signal 650 is an electrogram indicative of atrial tachyarrhythmia, arrhythmia classifier 730 classifies the atrial tachyarrhythmia as AF if $\Gamma_I$ is below a predetermined threshold $\gamma_I$ or if SampEn$_I$ exceeds a predetermined threshold $\theta_I$ and as AFL if $\Gamma_I$ exceeds $\gamma_I$ or if SampEn$_I$ is below $\theta_I$. In another specific embodiment, cardiac signal 650 is an electrogram indicative of ventricular tachyarrhythmia, arrhythmia classifier 730 classifies the ventricular tachyarrhythmia as VF if $\Gamma_I$ is below a predetermined threshold $\gamma_I$ or if SampEn$_I$ exceeds a predetermined threshold $\theta_I$ and as VT if $\Gamma_I$ exceeds $\gamma_I$ or if SampEn$_I$ is below $\theta_I$.

Arrhythmia Classification Based on Complexity Sample Entropy (SampEn$_C$)

Figure 8:
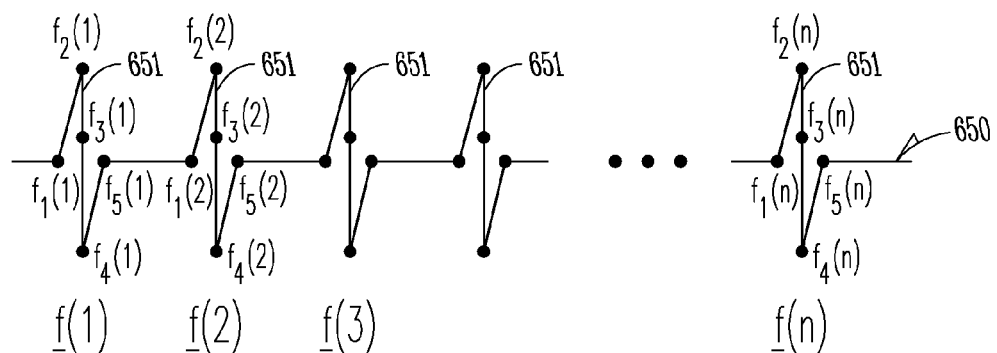
FIG. 8 illustrates an embodiment of a method for sampling a cardiac signal for analyzing morphological complexity of the cardiac signal using sample entropy.

FIG. 8 illustrates an embodiment of a method for sampling cardiac signal 650 for analyzing the morphological complexity of the cardiac signal using sample entropy. For each of n heart beats in cardiac signal 650, a set of morphological features are extracted. In one embodiment, a fiducial point that is a characteristic point present in each heart beat is used as a time reference point to temporally align the n heart beats, and the locations for the set of morphological features in all the heart beats are temporally aligned. In one embodiment, each morphological feature is represented by the amplitude measured at the location of that morphological feature on cardiac signal 650. The extracted sets of morphological features are represented by feature vectors $\underline{f}(1), \underline{f}(2), \ldots \underline{f}(n)$. As shown in FIG. 8 for illustrative purpose only, $\underline{f}(i)=[\underline{f}_1(i), \underline{f}_2(i), \underline{f}_3(i), \underline{f}_4(i), \underline{f}_5(i)]$. In general, $\underline{f}(i)=[\underline{f}_1(i), \underline{f}_2(i), \ldots \underline{f}_p(i)]$, where p is the number of features extracted from each heart beat.

Figure 9:
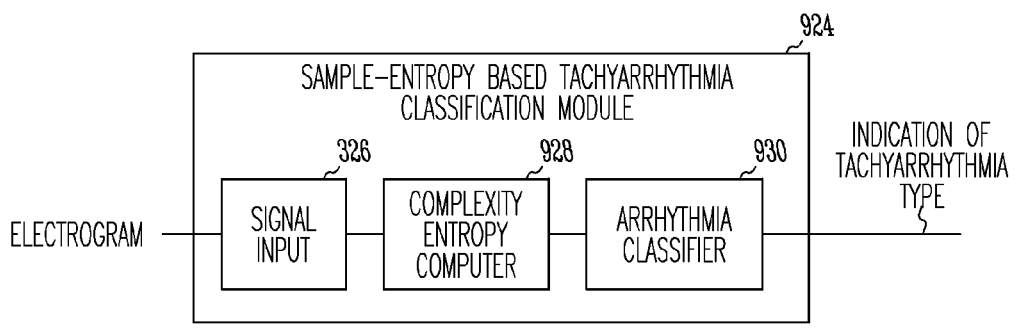
FIG. 9 is a block diagram illustrating another embodiment of the sample entropy-based tachyarrhythmia classification module.

FIG. 9 is a block diagram illustrating a sample entropy-based tachyarrhythmia classification module 924. Sample entropy-based tachyarrhythmia classification module 924 is another specific embodiment of sample entropy-based tachyarrhythmia classification module 224 and classifies tachyarrhythmias by analyzing the morphological complexity of cardiac signal 650. Sample entropy-based tachyarrhythmia classification module 924 includes signal input 326, a complexity entropy computer 928, and an arrhythmia classifier 930. Complexity entropy computer 928 is a specific embodiment of irregularity analyzer 328 and includes a sample entropy computer that performs method 400 by using the feature vectors $\underline{f}(1), \underline{f}(2), \ldots \underline{f}(n)$ as sample points u(1), u(2), . . . u(n). The resultant complexity $\Gamma$ ($\Gamma_C$) or complexity sample entropy (SampEn$_C$) indicates the degree of morphological complexity of cardiac signal 650. Arrhythmia classifier 930 classifies the tachyarrhythmia indicated in cardiac signal 650 as one of tachycardia and fibrillation based on $\Gamma_C$ or SampEn$_C$. In one embodiment, cardiac signal 650 is indicative of tachyarrhythmia, arrhythmia classifier 930 classifies the tachyarrhythmia as fibrillation if $\Gamma_C$ is below a predetermined threshold $\gamma_C$ or if SampEn exceeds a predetermined threshold $\theta_C$ and as tachycardia if $\Gamma_C$ exceeds $\gamma_C$ or if SampEn$_C$ is below $\theta_C$. In a specific embodiment, cardiac signal 650 is an electrogram indicative of atrial tachyarrhythmia, arrhythmia classifier 930 classifies the atrial tachyarrhythmia as AF if $\Gamma_C$ is below a predetermined threshold $\gamma_C$ or if SampEn$_C$ exceeds a predetermined threshold $\theta_C$ and as AFL if $\Gamma_C$ exceeds $\gamma_C$ or if SampEn$_C$ is below $\theta_C$. In another specific embodiment, cardiac signal 650 is an electrogram indicative of ventricular tachyarrhythmia, arrhythmia classifier 930 classifies the ventricular tachyarrhythmia as VF if $\theta_C$ is below a predetermined threshold $\gamma_C$ or if SampEn$_C$ exceeds a predetermined threshold $\theta_C$ and as VT if $\Gamma_C$ exceeds $\gamma_C$ or if SampEn$_C$ is below $\theta_C$.

Arrhythmia Classification Based on SampEn$_I$ and SampEn$_C$

Figure 10:
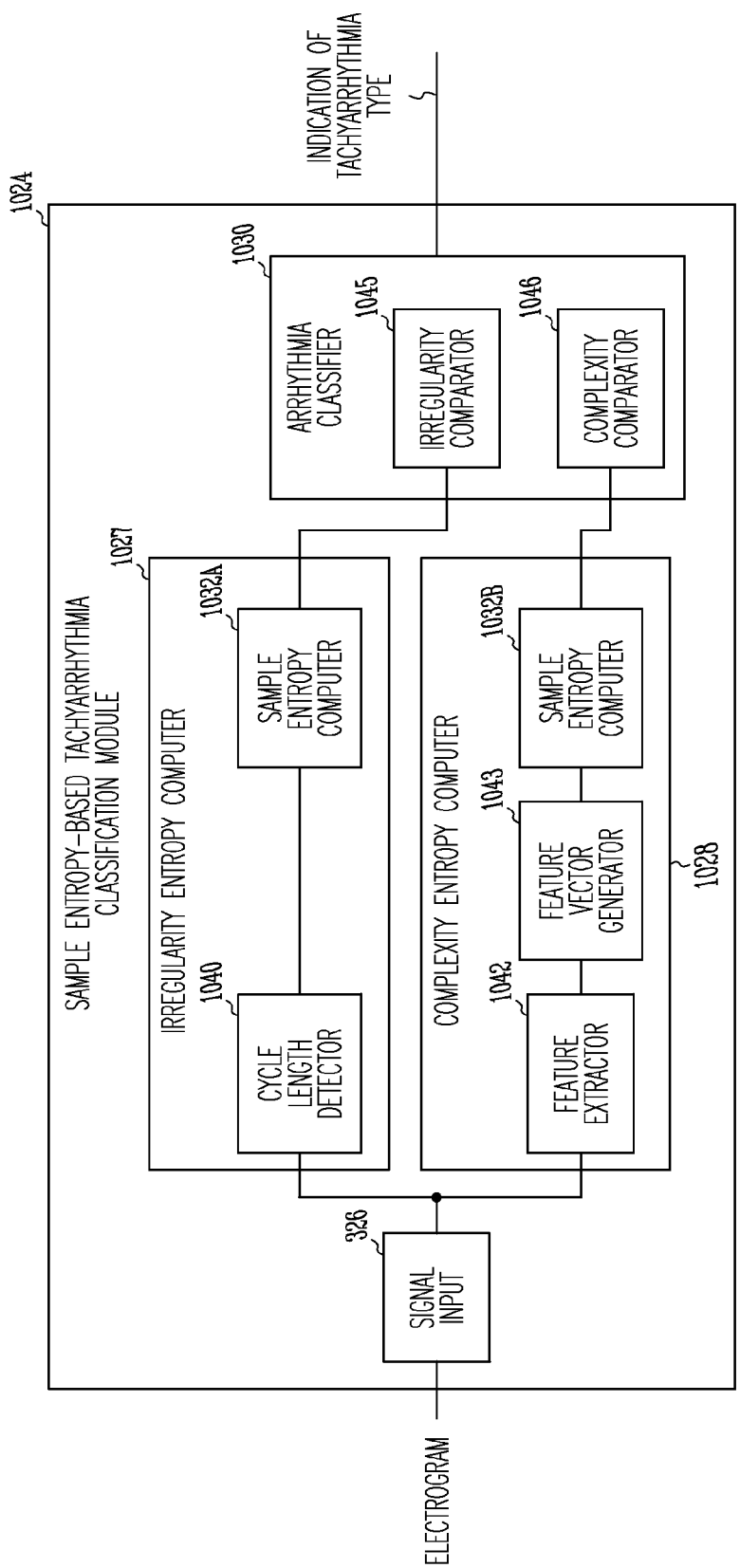
FIG. 10 is a block diagram illustrating another embodiment of the sample entropy-based tachyarrhythmia classification module.

FIG. 10 is a block diagram illustrating a sample entropy-based tachyarrhythmia classification module 1024, which is a specific embodiment of sample entropy-based tachyarrhythmia classification module 224 as well as a specific embodiment of arrhythmia classification module 324. Sample entropy-based tachyarrhythmia classification module 1024 includes signal input 326, an irregularity entropy computer 1027, a complexity computer 1028, and an arrhythmia classifier 1030.

Irregularity entropy computer 1027 is a specific embodiment of irregularity entropy computer 727. In one embodiment, irregularity entropy computer 1027 computes $\Gamma_I$ as an irregularity parameter indicative of the cycle length irregularity of the cardiac signal received by signal input 326. The parameter $\Gamma_I$ is related to SampEn$_I$ by SampEn$_I$=−ln$\Gamma_I$. Irregularity entropy computer 1027 includes a cycle length detector 1040 and a sample entropy computer 1032A. Cycle length detector 1040 measures $n_1$ successive cycle lengths, d(1), d(2), . . . d($n_1$), from the cardiac signal. For the purpose of calculating $\Gamma_I$, in one embodiment, the number of samples $n_1$ is a predetermined number in a range of approximately 20 to 50, with approximately 20 being a specific example. In another embodiment, the $n_1$ successive cycle lengths is measured during a predetermined duration $t_1$. The number $n_1$ is therefore a function of $t_1$ and the heart rate, given as $n_1 \approx R \cdot t_1 / 60$, wherein R is the heart rate in beats per minute (bpm) and $t_1$ is given in seconds. Duration $t_1$ is in a range of approximately 5 seconds to 20 seconds, with approximately 10 seconds being a specific example. In another embodiment, $n_1$ or $t_1$ is user-programmable. Sample entropy computer 1032A includes sample entropy computer 532 to compute $\Gamma$ using u(1), u(2), . . . u(n), where n=$n_1$, $\Gamma_I$=$\Gamma$, and u(1)=d(1), u(2)=d(2), . . . u($n_1$)=d($n_1$). For the purpose of calculating $\Gamma_I$, the signal segment length m is a predetermined number in a range of approximately 2 to 5, with approximately 3 being a specific example, and the threshold r is a predetermined threshold in a range of approximately 0 to 1, with approximately 0.5 being a specific example. In one embodiment, m and/or r are user-programmable. In one embodiment, irregularity entropy computer 1027 further computes SampEn$_I$ as the irregularity parameter by using that relationship SampEn$_I$=−ln$\Gamma_I$.

Complexity entropy computer 1028 is a specific embodiment of complexity entropy computer 928. In one embodiment, complexity entropy computer 1028 computes $\Gamma_C$ as an complexity parameter indicative of the morphological complexity of the cardiac signal received by signal input 326. The complexity parameter $\Gamma_I$ is related to $SampEn_C$ by $SampEn_C = -\ln\Gamma_C$. Complexity entropy computer 1028 includes a feature extractor 1042, a feature vector generator 1043, and a sample entropy computer 1032B. Feature extractor 1042 extracts p morphological features, $f_1(i), f_2(i), \ldots f_p(i)$, from each heart beat i of $n_2$ heart beats in the cardiac signal, where $1 \leq i \leq n_2$. For the purpose of calculating $\Gamma_C$, in one embodiment, the number of samples $n_2$ is a predetermined number in a range of approximately 10 to 50, with approximately 10 being a specific example. In another embodiment, the $n_2$ successive cycle lengths is measured during a predetermined duration $t_2$. The number $n_2$ is therefore a function of $t_2$ and the heart rate, given as $n_2 \approx R \cdot t_2/60$, wherein R is the heart rate in bpm and $t_2$ is given in seconds. Duration $t_2$ is in a range of approximately 5 seconds to 20 seconds, with approximately 5 seconds being a specific example. In another embodiment, $n_2$ or $t_2$ is user-programmable. The number of morphological features p is a predetermined number in a range of approximately 4 to 10, with approximately 5 being a specific example. Feature vector generator 1043 produces $n_2$ feature vectors associated with $n_2$ successive heart beats, $\underline{f}(1), \underline{f}(2), \ldots \underline{f}(n_2)$, where $\underline{f}(i) = [f_1(i), f_2(i), \ldots f_p(i)]$ for each $1 \leq i \leq n_2$. Sample entropy computer 1032B includes sample entropy computer 532 to compute $\Gamma$ using $u(1), u(2), \ldots u(n)$, where $n=n_2$, $\Gamma_C=\Gamma$, and $u(1)=\underline{f}(1), u(2)=\underline{f}(2), \ldots u(n_2)=\underline{f}(n_2)$. For the purpose of calculating $\Gamma_C$, the signal segment length m is a predetermined number in a range of approximately 2 to 5, with approximately 3 being a specific example, and the threshold r is a predetermined threshold in a range of approximately 0 to 1, with approximately 0.7 being a specific example. In one embodiment, m and/or r are user-programmable. In one embodiment, complexity entropy computer 1028 further computes $SampEn_C$ as the complexity parameter by using that relationship $SampEn_C = -\ln\Gamma_C$.

Arrhythmia classifier 1030 is a specific embodiment of arrhythmia classifier 330 and includes an irregularity comparator 1045 and a complexity comparator 1046. Irregularity comparator 1045 compares the irregularity parameter to a predetermined irregularity threshold and indicates a detection of irregularity based on an outcome of the comparison. Complexity comparator 1046 compares the complexity parameter to a predetermined complexity threshold and indicates a detection of complexity based on an outcome of the comparison. Arrhythmia classifier 1030 classifies a tachyarrhythmia episode indicated by the cardiac signal based on whether the detection of irregularity and/or the detection of complexity are indicated. In one embodiment, arrhythmia classifier 1030 classifies the tachyarrhythmia episode as fibrillation if at least one of the detection of irregularity and the detection of complexity is indicated and as tachycardia if none of the detection of irregularity and the detection of complexity is indicated.

In a specific embodiment, arrhythmia classifier 1030 classifies the tachyarrhythmia episode indicated by the cardiac signal based $\Gamma_I$ and $\Gamma_C$. Irregularity comparator 1045 compares $\Gamma_I$ to a predetermined irregularity threshold $\gamma_I$ and indicates a detection of irregularity if $\Gamma_I$ is below $\gamma_I$. Complexity comparator 1046 compares $\Gamma_C$ to a predetermined complexity threshold $\gamma_C$ and indicates a detection of complexity if $\Gamma_C$ is below $\gamma_C$. In another specific embodiment, arrhythmia classifier 1030 classifies the tachyarrhythmia episode indicated by the cardiac signal based on $SampEn_I$ and $SampEn_C$. Irregularity comparator 1045 compares $SampEn_I$ to a predetermined irregularity entropy threshold $\theta_I$ and indicates a detection of irregularity if $SampEn_I$ exceeds $\theta_I$. Complexity comparator 1046 compares $SampEn_C$ to a predetermined complexity entropy threshold $\theta_C$ and indicates a detection of complexity if $SampEn_C$ exceeds $\theta_C$.

In a specific embodiment, in which the cardiac signal is indicative of an atrial tachyarrhythmia episode, arrhythmia classifier 1030 classifies the atrial tachyarrhythmia episode as AF if at least one of the detection of irregularity and the detection of complexity is indicated and as AFL if none of the detection of irregularity and the detection of complexity is indicated. In another specific embodiment, in which the cardiac signal is indicative of a ventricular tachyarrhythmia episode, arrhythmia classifier 1030 classifies the ventricular tachyarrhythmia episode as VF if at least one of the detection of irregularity and the detection of complexity is indicated and to classify the arrhythmia episode as VT if none of the detection of irregularity and the detection of complexity is indicated.

Figure 11:
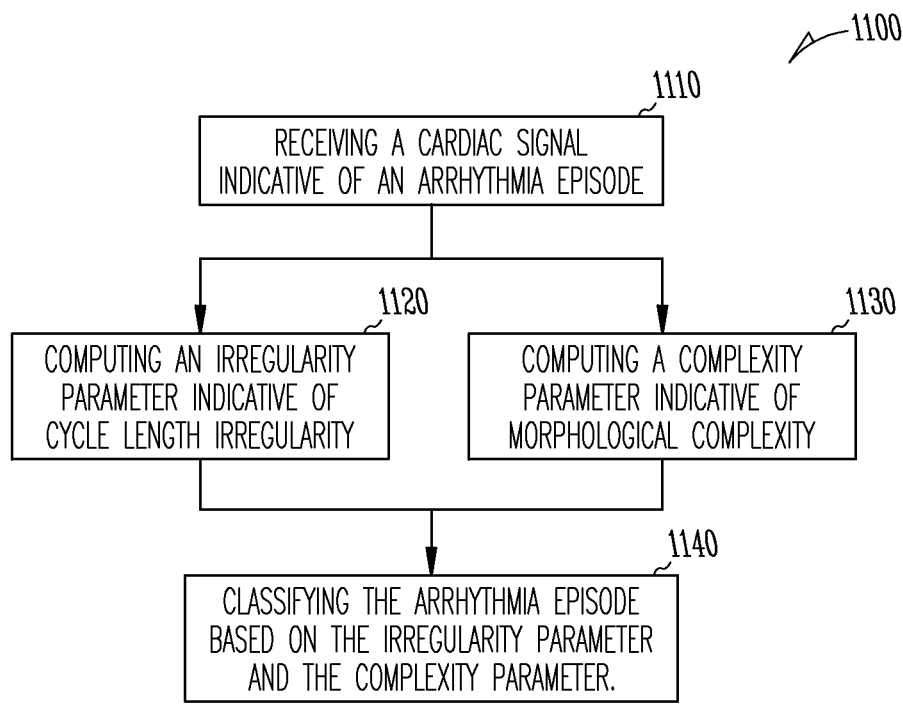
FIG. 11 is a flow chart illustrating an embodiment of a method for classifying tachyarrhythmias based on cycle length irregularity and morphological complexity.

FIG. 11 is a flow chart illustrating an embodiment of a method 1100 for classifying tachyarrhythmias based on cycle length irregularity and morphological complexity of a cardiac signal. In one embodiment, method 1100 is performed by arrhythmia classification module 324.

A cardiac signal indicative of an arrhythmia episode is received at 1110. An irregularity parameter indicative of the degree of cycle length irregularity of the cardiac signal is computed at 1120. A complexity parameter indicative of the degree of morphological complexity of the cardiac signal is computed at 1130. In one embodiment, steps 1120 and 1130 are performed substantially simultaneously. In another embodiment, steps 1120 and 1130 are performed sequentially. The arrhythmia episode is classified based on the irregularity parameter and the complexity parameter at 1140.

Figure 12:
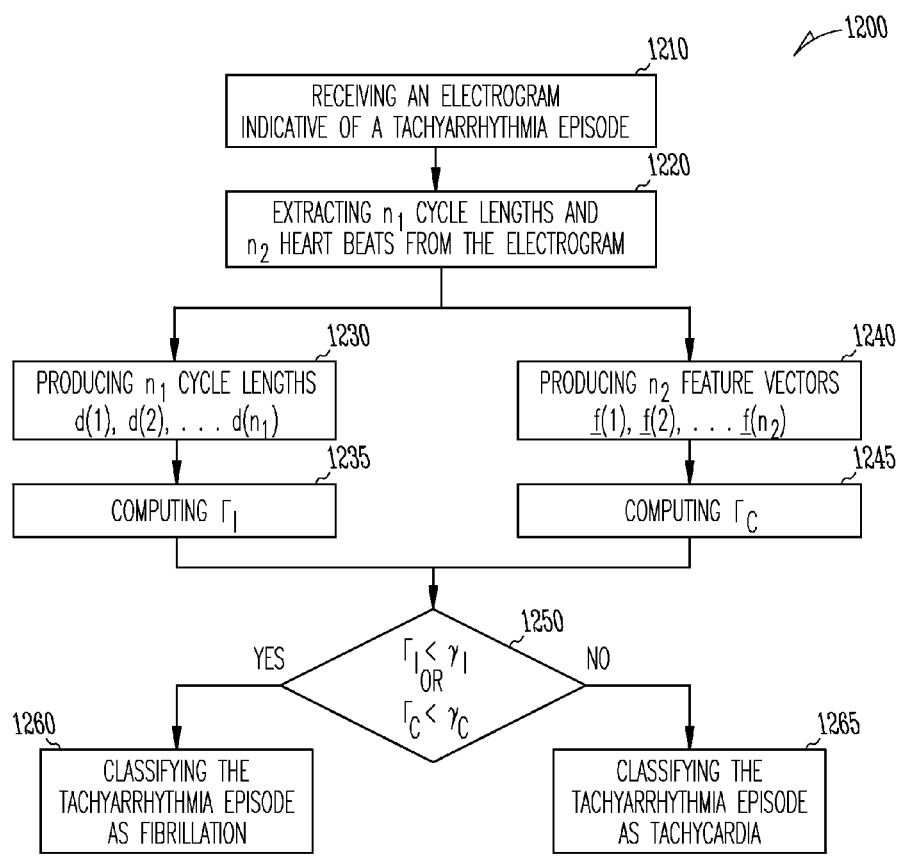
FIG. 12 is a flow chart illustrating an embodiment of the method for classifying tachyarrhythmias using sample entropy.

FIG. 12 is a flow chart illustrating an embodiment of a method 1200 for classifying tachyarrhythmias using sample entropy. Method 1200 is a specific embodiment of method 1100. In one embodiment, method 1200 is performed by sample entropy-based tachyarrhythmia classification module 1024.

A cardiac signal indicative of a tachyarrhythmia episode is received at 1210. In one embodiment, the cardiac signal is an electrogram indicative of an atrial tachyarrhythmia episode. In another embodiment, the cardiac signal is an electrogram indicative of a ventricular tachyarrhythmia episode.

A total number of $n_1$ cycle lengths and a total number of $n_2$ heart beats are extracted from the cardiac signal at 1220. The $n_1$ cycle lengths and $n_2$ heart beats are extracted from a segment of the cardiac signal based on which the tachyarrhythmia episode is to be classified. The $n_1$ cycle lengths are used to produce an irregularity parameter indicative of the cycle length irregularity of the cardiac signal. The $n_2$ heart beats are used to produce a complexity parameter indicative of the morphology complexity of the cardiac signal.

To produce the irregularity parameter, $n_1$ cardiac cycle lengths, $d(1), d(2), d(n_1)$, are produced at 1230 by measuring from the cardiac signal, and a parameter $\Gamma_I$ is computed at 1235 using method 400, which calculates $\Gamma$ using n sample points, $u(1), u(2), \ldots u(n)$. For calculating $\Gamma_I$ using method 400, $n=n_1$, $m=m_1$, and $r=r_1$ (wherein $n_1, m_1,$ and $r_1$ are chosen for calculating $\Gamma_I$), $\Gamma_I=\Gamma$, and $u(1)=d(1), u(2)=d(2), \ldots u(n_1)=d(n_1)$. The parameter $\Gamma_I$ is the irregularity parameter.

To produce the complexity parameter, $n_2$ feature vectors, $\underline{f}(1), \underline{f}(2), \ldots \underline{f}(n_2)$, are produced at 1240 by extracting p morphological features, $f_1(i), f_2(i), \ldots f_p(i)$, from heart beat i for the $n_2$ heart beats in the cardiac signal, and a parameter $\Gamma_C$ is computed at 1245 using method 400, which calculates $\Gamma$ using n sample points, $u(1), u(2), \ldots u(n)$. For calculating $\Gamma_C$ using method 400, $n=n_2$, $m=m_2$, and $r=r_2$ (wherein $n_2, m_2,$ and $r_2$ are chosen for calculating $\Gamma_C$), $\Gamma_C=\Gamma$, and $u(1)=\underline{f}(1)$, $u(2)=\underline{f}(2)$, ... $u(n_2)=\underline{f}(n_2)$. The parameter $\Gamma_C$ is the complexity parameter.

In one embodiment, as illustrated in FIG. 12, the irregularity parameter, $\Gamma_I$, is compared to a predetermined irregularity threshold $\gamma_I$, and the complexity parameter, $\Gamma_C$, is compared to a predetermined complexity threshold $\gamma_C$, at 1250. If at least one of $(\Gamma_I<\gamma_I)$ and $(\Gamma_C<\gamma_C)$ is true, the tachyarrhythmia episode is classified as fibrillation at 1260. If none of $(\Gamma_I<\gamma_I)$ and $(\Gamma_C<\gamma_C)$ is true, the tachyarrhythmia episode is classified as tachycardia at 1265. In a specific embodiment, in which the cardiac signal is the electrogram indicative of the atrial tachyarrhythmia episode, if at least one of $(\Gamma_I<\gamma_I)$ and $(\Gamma_C<\gamma_C)$ is true, the atrial tachyarrhythmia episode is classified as AF at 1260. If none of $(\Gamma_I<\gamma_I)$ and $(\Gamma_C<\gamma_C)$ is true, the atrial tachyarrhythmia episode is classified as AFL at 1265. In another specific embodiment, in which the cardiac signal is the electrogram indicative of the ventricular tachyarrhythmia episode, if at least one of $(\Gamma_I<\gamma_I)$ and $(\Gamma_C<\gamma_C)$ is true, the ventricular tachyarrhythmia episode is classified as VF at 1260. If none of $(\Gamma_I<\gamma_I)$ and $(\Gamma_C<\gamma_C)$ is true, the ventricular tachyarrhythmia episode is classified as VT at 1265.

In another embodiment, an index I is generated at 1250 as a function of $\Gamma_I$ and $\Gamma_C$ and compared to a predetermined threshold k. That is, $I=f(\Gamma_I, \Gamma_C)$, where f is a linear or nonlinear function. In a specific embodiment, the tachyarrhythmia episode is classified as fibrillation at 1260 if I exceeds k and as tachycardia at 1265 if I does not exceed k. In another specific embodiment, the tachyarrhythmia episode is classified as fibrillation at 1260 if I does not exceed k and as tachycardia at 1265 if I exceeds k.

Method 1200 as illustrated in FIG. 12 was applied to classify an atrial tachyarrhythmia episode using a cardiac signal recorded during a known AFL episode and another cardiac signal recorded during a known AF episode. Using $t_1=15$ seconds, $m_1=2$, and $r_1=0.25$ to compute $\Gamma_I$ for both cardiac signals, the $\Gamma_I$ associated with AFL is 0.5278, and the $\Gamma_I$ associated with AF is 0.4717. Using $t_2=15$ seconds, $m_2=3$, and $r_2=0.75$ to compute $\Gamma_I$ for both cardiac signals, the $\Gamma_C$ associated with AFL is 0.6835, and the $\Gamma_C$ associated with AF is 0.2500.

Figure 13:
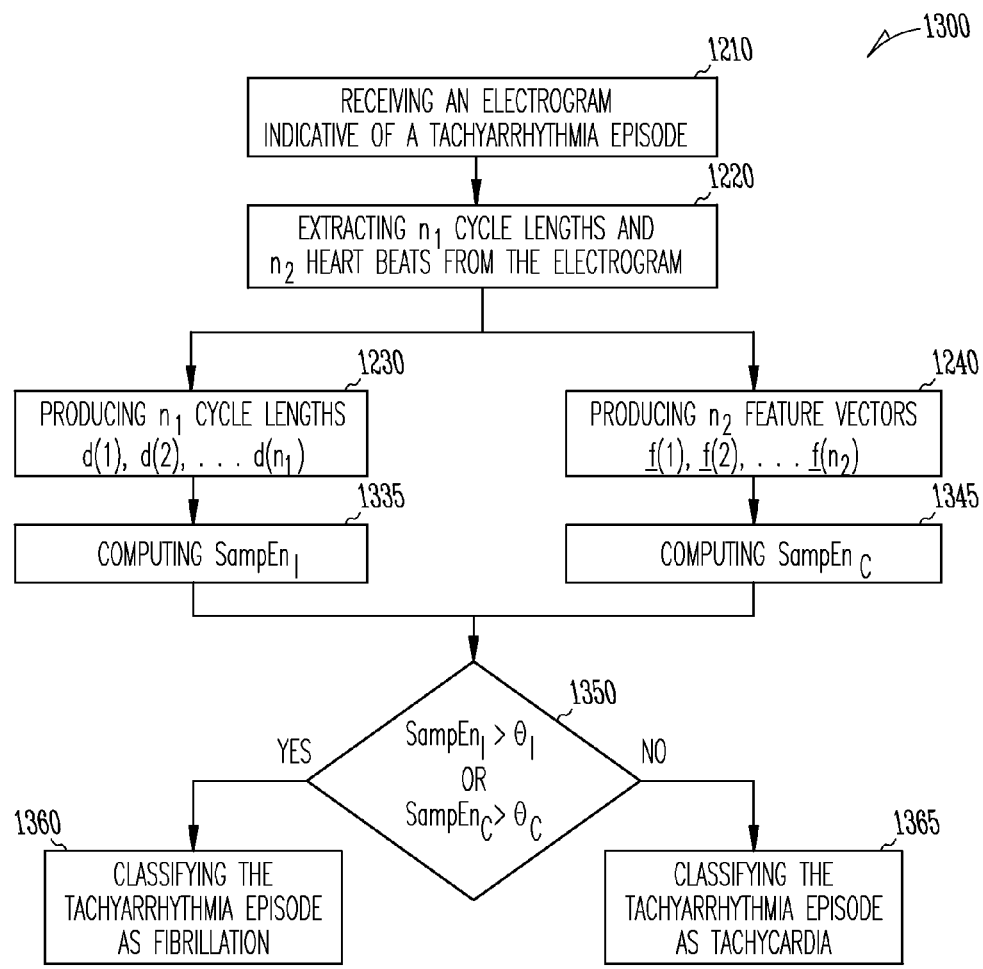
FIG. 13 is a flow chart illustrating another embodiment of the method for classifying tachyarrhythmias using sample entropy.

FIG. 13 is a flow chart illustrating a method 1300 for classifying tachyarrhythmias using sample entropy. Method 1300 is a specific embodiment of method 1100. In one embodiment, method 1200 is performed by sample entropy-based tachyarrhythmia classification module 1024. Method 1300 differs from method 1200 in that SampEn, instead of $\Gamma$, is used for classifying tachyarrhythmias. That is, the parameter $SampEn_I$ is the irregularity parameter, and the parameter $SampEn_C$ is the complexity parameter. As illustrated in FIG. 10, methods 1300 and 1200 both include steps 1210, 1220, 1230, and 1240.

The irregularity parameter, $SampEn_I$, is computed at 1335 using method 400, which calculates SampEn using n sample points, $u(1), u(2), \ldots u(n)$. For calculating $SampEn_I$, using method 400, $n=n_1, m=m_1$, and $r=r_1$ (wherein $n_1, m_1$, and $r_1$ are chosen for calculating $SampEn_I$), $SampEn_I=SampEn$, and $u(1)=d(1), u(2)=d(2), \ldots u(n_1)=d(n_1)$.

The complexity parameter, $SampEn_C$, is computed at 1345 using method 400, which calculates SampEn using n sample points, $u(1), u(2), \ldots u(n)$. For calculating $SampEn_C$ using method 400, $n=n_2, m=m_2$, and $r=r_2$ (wherein $n_2, m_2$, and $r_2$ are chosen for calculating $SampEn_C$), $SampEn_C=SampEn$, and $u(1)=\underline{f}(1), u(2)=\underline{f}(2), \ldots u(n_2)=\underline{f}(n_2)$.

In one embodiment, as illustrated in FIG. 13, the irregularity parameter, $SampEn_I$, is compared to a predetermined irregularity threshold $\theta_I$, and the complexity parameter, $SampEn_C$, is compared to a predetermined complexity threshold $\theta_I$, at 1350. If at least one of $(SampEn_I>\theta_I)$ and $(SampEn_C>\theta_C)$ is true, the tachyarrhythmia episode is classified as fibrillation at 1360. If none of $(SampEn_I>\theta_I)$ and $(SampEn_C>\theta_C)$ is true, the tachyarrhythmia episode is classified as tachycardia at 1365. In a specific embodiment, in which the cardiac signal is the electrogram indicative of the atrial tachyarrhythmia episode, if at least one of $(SampEn_I>\theta_I)$ and $(SampEn_C>\theta_C)$ is true, the atrial tachyarrhythmia episode is classified as AF at 1260. If none of $(SampEn_I>\theta_C)$ and $(SampEn_C>\theta_C)$ is true, the atrial tachyarrhythmia episode is classified as AFL at 1265. In another specific embodiment, in which the cardiac signal is the electrogram indicative of the ventricular tachyarrhythmia episode, if at least one of $(SampEn_I>\theta_I)$ and $(SampEn_C>\theta_C)$ is true, the ventricular tachyarrhythmia episode is classified as VF at 1260. If none of $(SampEn_I>\theta_I)$ and $(SampEn_C>\theta_C)$ is true, the ventricular tachyarrhythmia episode is classified as VT at 1265.

In another embodiment, an index I is generated at 1350 as a function of $SampEn_I$ and $SampEn_C$ and compared to a predetermined threshold k. That is, $I=f(SampEn_I, SampEn_C)$, where f is a linear or nonlinear function. In a specific embodiment, the tachyarrhythmia episode is classified as fibrillation at 1360 if I exceeds k and as tachycardia at 1365 if I does not exceed k. In another specific embodiment, the tachyarrhythmia episode is classified as fibrillation at 1360 if I does not exceed k and as tachycardia at 1365 if I exceeds k.

In General

Sample entropy is specifically discussed in this document as an example for analyzing the cycle length irregularity and/or morphological complexity of a cardiac signal. It is to be understood, however, that other parameters indicative of the cycle length irregularity and/or morphological complexity are also useable in classifying arrhythmias according the present subject matter. Such other parameters include, but are not limited to, parameters representing or related to approximate entropy. For example, an irregularity approximate entropy, $ApEn_I$, or a parameter related to the $ApEn_I$, can be computed and used as the irregularity parameter discussed in this document; a complexity approximate entropy, $ApEn_C$, or a parameter related to the $ApEn_C$, can be computed and used as the complexity parameter discussed in this document.

It is to be understood that the above detailed description is intended to be illustrative, and not restrictive. For example, various embodiments of system and method for cardiac arrhythmia classification as discussed in this document are not limited to applications in an implantable medical device, but may be incorporated into any arrhythmia analysis system, such as a computer program for analyzing pre-collected cardiac data. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system for classifying cardiac arrhythmias, the system comprising:
   a signal input to receive a cardiac signal indicative of a detected arrhythmia episode;
   an irregularity analyzer and a complexity analyzer, coupled to the signal input, the irregularity analyzer including an irregularity entropy computer adapted to compute an irregularity parameter $\Gamma_I$ indicative of a degree of cycle length irregularity of the cardiac signal, $\Gamma_I$ related to an irregularity sample entropy ($SampEn_I$) indicative of the degree of cycle length irregularity of the cardiac signal, wherein SampEn$_I$=−ln$\Gamma_I$, the complexity analyzer including a complexity entropy computer adapted to compute a complexity parameter $\Gamma_C$ indicative of a degree of morphological complexity of the cardiac signal, $\Gamma_C$ related to a complexity sample entropy (SampEn$_C$) indicative of the degree of morphological complexity of the cardiac signal, wherein SampEn$_C$=−ln$\Gamma_C$; and an arrhythmia classifier coupled to the irregularity analyzer and the complexity analyzer, the arrhythmia classifier adapted to classify the detected arrhythmia episode using the irregularity parameter and the complexity parameter.

2. The system of claim 1, wherein the arrhythmia classifier comprises an irregularity comparator adapted to compare $\Gamma_I$ to a predetermined irregularity threshold ($\gamma_I$) and indicate a detection of irregularity if $\Gamma_I$ is below $\gamma_I$, and is adapted to classify the detected arrhythmia episode as fibrillation if the detection of irregularity is indicated and to classify the detected arrhythmia episode as tachycardia if the detection of irregularity is not indicated.

3. The system of claim 1, wherein the irregularity entropy computer is further adapted to compute SampEn$_I$ using $\Gamma_I$, and wherein the arrhythmia classifier comprises an irregularity comparator adapted to compare SampEn$_I$ to a predetermined irregularity entropy threshold ($\theta_I$) and indicate a detection of irregularity if SampEn$_I$ exceeds $\theta_I$, and is adapted to classify the detected arrhythmia episode as fibrillation if the detection of irregularity is indicated and to classify the detected arrhythmia episode as tachycardia if the detection of irregularity is not indicated.

4. The system of claim 1, wherein the complexity analyzer comprises a complexity comparator adapted to compare $\Gamma_C$ to a predetermined complexity threshold ($\gamma_C$) and indicate a detection of complexity if $\Gamma_C$ is below $\gamma_C$, and wherein the arrhythmia classifier is adapted to classify the detected arrhythmia episode as fibrillation if the detection of complexity is indicated and to classify the detected arrhythmia episode as tachycardia if the detection of complexity is not indicated.

5. The system of claim 1, wherein the complexity entropy compute is further adapted to compute SampEn$_C$ using $\Gamma_C$, and wherein the arrhythmia classifier comprises an complexity comparator adapted to compare SampEn$_C$ to a predetermined complexity entropy threshold ($\theta_C$) and indicate a detection of complexity if SampEn$_C$ exceeds $\theta_C$, and is adapted to classify the detected arrhythmia episode as fibrillation if the detection of complexity is indicated and to classify the detected arrhythmia episode as tachycardia if the detection of complexity is not indicated.

6. The system of claim 1, wherein the arrhythmia classifier comprises:

an irregularity comparator adapted to compare $\Gamma_I$ to a predetermined irregularity threshold ($\gamma_I$) and indicate a detection of irregularity if $\Gamma_I$ is below $\gamma_I$; and a complexity comparator adapted to compare $\Gamma F_C$ to a predetermined complexity threshold ($\gamma_C$) and indicate a detection of complexity if $\Gamma_C$ is below $\gamma_C$, and wherein the arrhythmia classifier is adapted to classify the detected arrhythmia episode as fibrillation if at least one of the detection of irregularity and the detection of complexity is indicated and to classify the detected arrhythmia episode as tachycardia if none of the detection of irregularity and the detection of complexity is indicated.

7. The system of claim 1, wherein the irregularity entropy computer is further adapted to compute SampEn$_I$ using $\Gamma_I$, wherein the complexity entropy computer is further adapted to compute SampEn$_C$ using $\Gamma_C$, and wherein the arrhythmia classifier comprises an irregularity comparator adapted to compare SampEn$_I$ to a predetermined irregularity entropy threshold ($\theta_I$) and indicate a detection of irregularity if SampEn$_I$ exceeds $\theta_I$ and a complexity, comparator adapted to compare SampEn$_C$ to a predetermined complexity entropy threshold ($\theta_C$) and indicate a detection of complexity if SampEn$_C$ exceeds $\theta_C$, and is adapted to classify the detected arrhythmia episode as fibrillation if at least one of the detection of irregularity and the detection of complexity is indicated and to classify the detected arrhythmia episode as tachycardia if none of the detection of irregularity and the detection of complexity is indicated.

8. The system of claim 7, further comprising:

a sensing circuit to sense an electrogram; and a tachyarrhythmia detector coupled to the sensing circuit, the tachyarrhythmia detector adapted to detect an atrial tachyarrhythmia episode using the electrogram, and wherein the arrhythmia classifier is adapted to classify the detected atrial tachyarrhythmia episode as atrial fibrillation if at least one of the detection of irregularity and the detection of complexity is indicated and to classify the detected atrial tachyarrhythmia episode as atrial flutter if none of the detection of irregularity and the detection of complexity is indicated.

9. The system of claim 7, further comprising:

a sensing circuit to sense an electrogram; and a tachyarrhythmia detector coupled to the sensing circuit, the tachyarrhythmia detector adapted to detect a ventricular tachyarrhythmia episode from the electrogram, and wherein the arrhythmia classifier is adapted to classify the detected ventricular tachyarrhythmia episode as ventricular fibrillation if at least one of the detection of irregularity and the detection of complexity is indicated and to classify the detected ventricular tachyarrhythmia episode as ventricular tachycardia if none of the detection of irregularity and the detection of complexity is indicated.

10. A method for classifying cardiac arrhythmias, the method comprising:

detecting an arrhythmia episode;

receiving a cardiac signal indicative of the arrhythmia episode;

computing an irregularity parameter indicative of a degree of cycle length irregularity of the cardiac signal and a complexity parameter indicative of a degree of morphological complexity of the cardiac signal, the irregularity parameter being an irregularity parameter $\Gamma_I$ related to an irregularity sample entropy (SampEn$_I$) indicative of the degree of cycle length irregularity of the cardiac signal, wherein SampEn$_I$=−ln$\Gamma_I$, the complexity parameter being a complexity parameter $\Gamma_C$ related to a complexity sample entropy (SampEn$_C$) indicative of the degree of morphological complexity of the cardiac signal, wherein SampEn$_C$=−ln$\Gamma_C$; and classifying the arrhythmia episode using the irregularity parameter and the complexity parameter.

11. The method of claim 10, comprising:

comparing $\Gamma_I$ to a predetermined irregularity threshold ($\gamma_I$);

indicating a detection of irregularity if $\Gamma_I$ is below $\gamma_I$; and classifying the arrhythmia episode as fibrillation if the detection of irregularity is indicated and as tachycardia if the detection of irregularity is not indicated.

12. The method of claim 10, wherein classifying the arrhythmia episode comprises:

computing SampEn$_I$ using $\Gamma_I$;

comparing SampEn$_I$ to a predetermined irregularity entropy threshold ($\theta_I$);

indicating a detection of irregularity if SampEn$_I$ exceeds θ$_I$; and classifying the arrhythmia episode as fibrillation if the detection of irregularity is indicated and as tachycardia if the detection of irregularity is not indicated.

13. The method of claim 10, comprising:

comparing Γ$_C$ to a predetermined complexity threshold (γ$_C$);

indicating a detection of irregularity if Γ$_C$ is below γ$_C$; and classifying the arrhythmia episode as fibrillation if the detection of complexity is indicated and as tachycardia if the detection of complexity is not indicated.

14. The method of claim 10, wherein classifying the arrhythmia episode comprises:

computing SampEn$_C$ using Γ$_C$;

comparing SampEn$_C$ to a predetermined complexity entropy threshold (θ$_C$);

indicating a detection of complexity if SampEn$_I$ exceeds θ$_C$; and classifying the arrhythmia episode as fibrillation if the detection of complexity and is indicated and as tachycardia if the detection of complexity is not indicated.

15. The method of claim 10, comprising:

comparing Γ$_I$ to a predetermined irregularity threshold (γ$_I$);

indicating a detection of irregularity if Γ$_I$ is below γ$_I$;

comparing Γ$_C$ to a predetermined complexity threshold (γ$_C$);

indicating a detection of irregularity if Γ$_C$ is below γ$_C$; and classifying the arrhythmia episode as fibrillation if at least one of the detection of irregularity and the detection of complexity is indicated and as tachycardia if none of the detection of irregularity and the detection of complexity is indicated.

16. The method of claim 10, wherein classifying the arrhythmia episode comprises:

computing SampEn$_I$ using Γ$_I$;

comparing SampEn$_I$ to a predetermined irregularity entropy threshold (θ$_I$);

indicating a detection of irregularity if SampEn$_I$ exceeds θ$_I$;

computing SampEn$_C$ using Γ$_C$;

comparing SampEn$_C$ to a predetermined complexity entropy threshold (θ$_C$);

indicating a detection of complexity if SampEn$_I$ exceeds θ$_C$; and classifying the arrhythmia episode as fibrillation if at least one of the detection of irregularity and the detection of complexity is indicated and as tachycardia if none of the detection of irregularity and the detection of complexity is indicated.

17. The method of claim 16, further comprising sensing an electrogram and detecting an atrial tachyarrhythmia episode using the electrogram, and wherein classifying the arrhythmia episode comprises discriminating between atrial flutter and atrial fibrillation.

18. The method of claim 16, further comprising sensing an electrogram and detecting a ventricular tachyarrhythmia episode using the electrogram, and wherein classifying the arrhythmia episode comprises discriminating between ventricular tachycardia and ventricular fibrillation.

* * * * *